US00PP22226P2

(12) United States Plant Patent
Korlipara

(10) Patent No.: US PP22,226 P2
(45) Date of Patent: Nov. 1, 2011

(54) ***HEUCHERA* PLANT NAMED 'TNMT'**

(50) Latin Name: ***Heuchera* spp.**
Varietal Denomination: TNMT

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,254

(22) Filed: May 11, 2010

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu
(74) *Attorney, Agent, or Firm* — Klarquist Sparkman, LLP

(57) ABSTRACT

A new and distinct hybrid of *Heuchera* plant characterized by medium sized, lobed, slightly ruffled leaves with a distinctive white veil, red gold to amber to khaki leaf color, and a small, mounding habit.

2 Drawing Sheets

Botanical denomination: *Heuchera* spp.

Variety designation: 'TNMT'.

Cross Reference to *Heuchera* 'Amber Waves' (U.S. Plant Pat. No. 13,348).

BACKGROUND OF THE INVENTION

The present invention relates to a new and distinct cultivar of *Heuchera* and given the name of 'TNMT'. *Heuchera* is in the family Saxifragaceae. *Heuchera* 'TNMT' originated from a whole plant mutation in tissue culture of *Heuchera* 'Amber Waves' (U.S. Plant Pat. No. 13,348). This whole plant was found in the production area of the nursery in Canby, Oreg., in a plant out of *Heuchera* 'Amber Waves'.

Compared to the parent, *Heuchera* 'Amber Waves', the new cultivar has leaves that are wavier and have a white veil rather than no veil.

This new *Heuchera* is uniquely distinguished by:

1. medium sized, lobed, slightly ruffled leaves with a distinctive white veil,
2. red gold to amber to khaki leaf color, and
3. small, mounding habit.

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
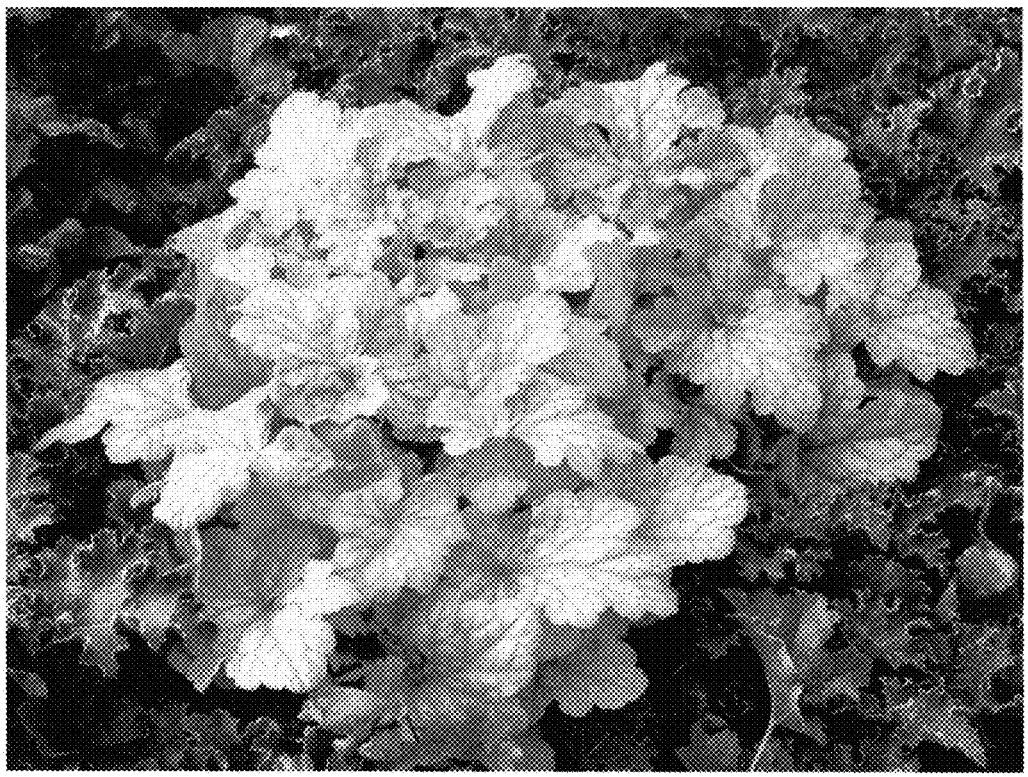
FIG. 1 shows a one-year-old plant of *Heuchera* 'TNMT' growing in the ground in shade in the garden in May in Canby, Oreg.
Figure 2:
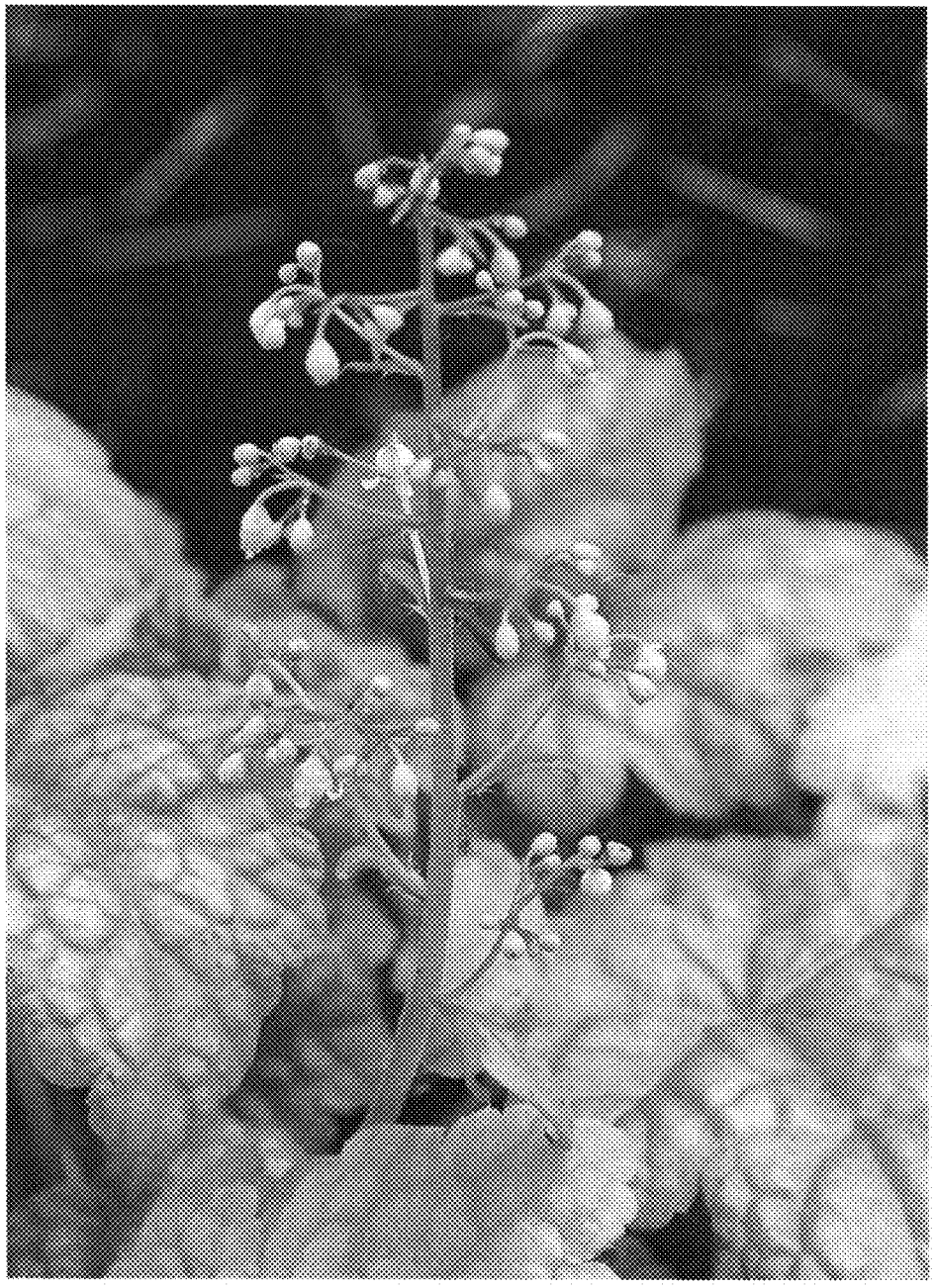
FIG. 2 shows the inflorescence of *Heuchera* 'TNMT'.

The following is a detailed description of the new *Heuchera* cultivar based on observations taken in May of eleven-month-old specimens growing in 4 inch pots in the greenhouse in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—19 cm tall from top of the foliage to the ground and 37 cm wide.
*Habit.*—Mounding from one main crown.
*Vigor.*—Excellent.

Leaf:

*Type.*—Simple.
*Arrangement.*—Rosette.
*Shape.*—Broadly ovate.
*Lobing /division.*—5 main lobes, the terminal is the longest; shallow secondary lobes, bottom two lobes often deeply cut.
*Venation.*—Palmate.
*Margins.*—Broadly crenate and undulate.
*Apex.*—Mucronulate.
*Base.*—Cordate, lobes strongly overlapping at the base.
*Blade size.*—Grows to 12 cm long and 12.5 cm wide.
*Texture.*—Leathery.
*Surface texture.*—Glandular on both sides.
*Petiole description.*—Grows to 14 cm long and 2 mm wide, glandular hairs, closest to Greyed Red 182B.
*Leaf color.*—Variable; topside, new spring leaves open with veiled Greyed Brown 199D with prominent reticulate veins Greyed Orange 166B, bottom side Greyed Purple 185A; mature leaves and summer leaves are veiled Greyed Yellow 162D with veins Yellow Green 152A, bottom side Greyed Purple 185D; older and winter leaves are Yellow Green 146B with some veiling Yellow Green 148D, bottom side Yellow Green 146B tinted Greyed Purple 185A.

Inflorescence:

*Size.*—Grows to 6 cm wide and 31 cm long.

*Type.*—Thyrse.

*Number of flowers per thyrse.*—About 90.

*Number of thyrse.*—2.

*Peduncle.*—About 52 cm long, 3 mm wide at base, Greyed Purple 185A, glandular hairs, with 3 to 4 cauline leaves, blades ovate, 5 lobed, grow to 4 cm long and 3.5 cm wide, crenate, mucronulate, cordate to attenuate, Greyed Orange 165B on top, 184B on bottom, petiolate lower leaves.

*Pedicel.*—Variable in size, with glandular hairs, Greyed Purple 185A.

*Bloom period.*—May through June in Canby, Oreg.

Flower bud:

*Size.*—2 mm wide and 3 mm long.

*Description.*—Glandular puberulent, ovoid, down facing.

*Color.*—Greyed Purple 186B on bottom half 186D on top half.

Flower:

*Type.*—Perfect.

*Shape.*—Campanulate.

*Size.*—4.5 mm long and 3 mm wide.

*Corolla description.*—5 in number, 1.5 mm long and 0.5 mm wide, spatulate, curled back, tip acute, margin entire, glabrous on top side, glandular on bottom side, White 155A.

*Calyx description.*—Campanulate, 3 mm long and 3 mm wide, with 5 lobes divided ⅓ way to the base, glandular hairs, tips obtuse, margin entire; Red Purple 62D with lobe tips Red Purple 61A.

*Stamen description.*—5 in number, filaments 2.7 mm long, White 155A, anthers 0.5 mm, Orange 26A, pollen Yellow Orange 20B.

*Pistil description.*—1, 2-beaked, 4 mm long; ovary 1.5 mm long, style 2.5 mm long, White 155A overall.

*Fragrance.*—None.

*Lastingness.*—Each thyrse blooms for about 3 weeks on the plant.

Fruit:

*Type.*—Two-beaked ovoid capsule.

*Fertility.*—Good.

*Color.*—Brown 200D.

Seed:

*Shape.*—Linear.

*Size.*—2 mm. long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

* * * * *